United States Patent [19]

Umezawa et al.

[11] Patent Number: 4,808,703

[45] Date of Patent: Feb. 28, 1989

[54] NOVEL 3-(4′-AMINOBUTYLAMINO) PROPYLAMINOBLEOMYCIN DERIVATIVES

[75] Inventors: Hamao Umezawa, Tokyo; Akio Fujii, Kamakura; Yasuhiko Muraoka, Tokyo; Tokuji Nakatani, Ina; Takeyo Fukuoka, Yono; Katsutoshi Takahashi, Tokyo, all of Japan

[73] Assignee: Zaidan Hojin Biseibutsu Kagaku Kenku Kai, Tokyo, Japan

[21] Appl. No.: 622,884

[22] Filed: Jun. 21, 1984

[30] Foreign Application Priority Data

Jun. 27, 1983 [JP] Japan .................. 58-114257

[51] Int. Cl.$^4$ .......................... C07C 103/52
[52] U.S. Cl. .................. 530/322; 536/16.8
[58] Field of Search .................. 536/168, 32; 260/112.5 R; 530/322

[56] References Cited

U.S. PATENT DOCUMENTS

Re. 30,451 12/1980 Umezawa et al. .......... 260/112.5 R
3,922,262 11/1975 Umezawa et al. .......... 260/112.5 R

OTHER PUBLICATIONS

Umezawa et al., *The Journal of Antibiotics,* Ser. A, 1966, pp. 200–209, 210–215, published in Japan.
Migrdichian, Organic Synthesis, vol. 1, 1957, p. 472 (published by Reinhol Publ. Corp.).

*Primary Examiner*—Johnnie R. Brown
*Assistant Examiner*—Elli Peselev
*Attorney, Agent, or Firm*—Henry C. Nields

[57] ABSTRACT

Disclosed is a 3-(4′-aminobutylamino) propylaminobleomycin having low pulmonary toxicity, which expressed by the following general formula $$[BX]-NH-(CH_2)_3-A-(CH_2)_4-B$$

wherein [BX] represents a residue remaining after removing a hydroxyl group from the carboxyl group of bleomycinic acid, A represents a group of the formula

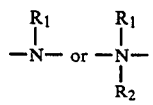

in which $R_1$ represents (i) a hydrogen atom, (ii) an alkyl group having 1 to 10 carbon atoms, or (iii) a methyl which may be substituted by at least one of a phenyl group and a cycloalkyl group having 5 to 13 carbon atoms, said substituents being each optionally further substituted more than one position by one or more substituents selected from the class consisting of a halogen atom, a lower alkyl group having 1 to 4 carbon atoms, a lower alkoxy group having 1 to 4 carbon atoms, and benzyloxy group; and $R_2$ represents a lower alkyl group having 1 to 4 carbon atoms or a benzyl group, B represents a group of the formula

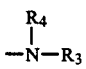

in which $R_3$ and $R_4$ each represents (i) a hydrogen atom, (ii) an alkyl group having 5 to 10 carbon atoms, or (iii) a methyl which may be substituted by at least one of a phenyl group and a cycloalkyl group, said substituents being each optionally further substituted more than one position by one or more substituents selected from the class consisting of a halogen atom, a lower alkyl group having 1 to 4 carbon atoms, a lower alkoxy group having 1 to 4 carbon atoms and a benzyloxy group, with the proviso that at least one of $R_3$ and $R_4$ is a group other than a hydrogen atom, and salt thereof.

6 Claims, No Drawings

3-(4'-AMINOBUTYLAMINO) PROPYLAMINOBLEOMYCIN DERIVATIVES

BACKGROUND OF THE INVENTION

This invention relates to novel aminopropylaminobleomycin derivatives.

Bleomycin is a carcinostatic antibiotic discovered in 1966 by Umezawa, one of the present inventors, and his colleagues (Umezawa et al., The Japanese Journal of Antibiotics, page 200, 1966). It is a water-soluble basic glycopeptide which is produced by *Streptomyces verticillus*, an Actinomycete, and which easily chelates one bivalent copper. This antibiotic that has hitherto been produced by the ordinary cultivation method and isolated includes 16 copper-containing bleomycins (e.g. Umezawa et al., The Japanese Journal of Antibiotics 19A, page 210, 1966). Among these bleomycins are A1, A2, A5, B2, demethyl-A2, etc. that are available as a copper-free mixture (hereinafter referred to as bleomycin complex). Currently, bleomycin complex is widely used in clinical practice to treat cancer, and achieved excellent results in the treatment of squamous cell carcinoma and other types of cancer such as skin cancer, cancer of the head and neck, pulmonary cancer, or malignant lympohoma.

U.S. Pat. Nos. 3,922,262 and Re. 30,451 also disclose various bleomycins.

Bleomycins, however, are markedly restricted in terms of methods to use them and so on, because they produce adverse reactions, such as pulmonary toxicity, depending on the ways of using them.

SUMMARY OF THE INVENTION

To reduce the above-mentioned untoward effects of bleomycins, such as pulmonary toxicity, the present inventors conducted a variety of studies, finding that the pulmonary toxicity of 3-(4'-aminobutylamino)-propylaminobleomycin (referred to hereinafter as $BLMA_5$) can be decreased remarkably by modifying its amino groups. This finding led them to accomplish the present invention.

Novel aminopropylaminobleomycin derivatives according to this invention (referred to hereinafter as $BLMA_5$ deriv.) include both copper-containing compounds and copper-free compounds and are expressed by the following general formula [I]

$$[BX]-NH-(CH_2)_3-A-(CH_2)_4-B \quad [I]$$

wherein [BX] represents a residue remaining after removing a hydroxyl group from the carboxyl group of bleomycinic acid of the following formula

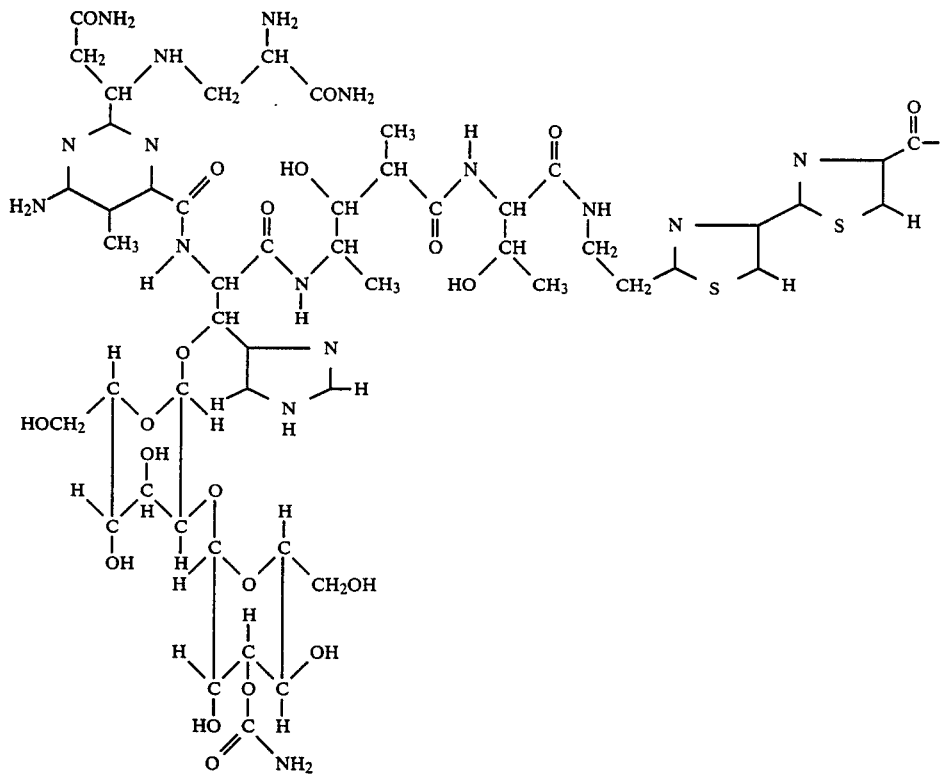

(chelated copper is omitted in the case of copper-containing compounds),

A represents a group of the formula

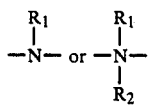

in which $R_1$ represents (i) a hydrogen atom, (ii) an alkyl group having 1 to 10 carbon atoms, or (iii) an methyl which may be substituted by at least one of a phenyl group and a cycloalkyl group having 5 to 13 carbon atoms, said substituents being each optionally further substituted more than one position by one or more substituents selected from the class consisting of a halogen atom; a lower alkyl group having 1 to 4 carbon atoms, a lower alkoxy group having 1 to 4 carbon atoms, and benzyloxy group; and R₂ represents a lower alkyl group having 1 to 4 carbon atoms or a benzyl group, B represents a group of the formula

in which R₃ and R₄ each represents (i) a hydrogen atom, (ii) an alkyl group having 5 to 10 carbon atoms, or (iii) an methyl which may be substituted by at least one of a phenyl group and a cycloalkyl group, said substituents being each optionally further substituted more than one position by one or more substituents selected from the class consisting of a halogen atom, a lower alkyl group having 1 to 4 carbon atoms, a lower alkoxy group having 1 to 4 carbon atoms, and a benzyloxy group, with the proviso that at least one of R₃ and R₄ is a group other than a hydrogen atom.

DETAILED DESCRIPTION OF THE INVENTION

In the above description, the lower alkyl groups are exemplified by methyl, ethyl, propyl, isopropyl, n-butyl, isobutyl, etc. Examples of the halogen atoms are fluorine, chlorine, bromine, etc. Examples of the cycloalkyl groups are cyclopentyl, cyclohexyl, cycloheptyl, cyclooctyl, cyclodecanyl, cycloundecanyl, etc. Examples of the lower alkoxy groups include methoxy, ethoxy, propoxy, butoxy, etc.

In the definition for A, the group of the formula

is exemplified by

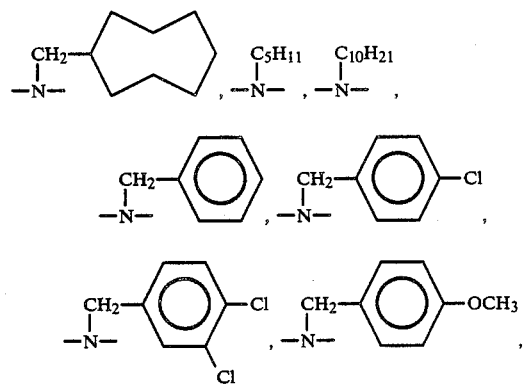

or the like, and the group expressed by the formula

is exemplified by

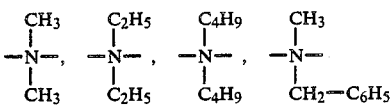

or the like.

The compounds of this invention are typified, for instance, by the compounds shown in Table 1.

TABLE 1

| Comp. No. | Compound | Abbreviation |
|---|---|---|
| 1 | 3-[N—benzyl-N—(4'-dibenzylaminobutyl)-amino]propylaminobleomycin | A5TBZ |
| 2 | 3-{[N—p-chlorobenzyl-N—[4'-bis(p-chlorobenzyl)aminobutyl]amino} propylaminobleomycin | A5TClBZ(p) |
| 3 | 3-{N—m,p-dichlorobenzyl-N—[4'-bis(m,p-dichlorobenzyl)aminobutyl]amino} propylaminobleomycin | A5TDClBZ (m,p) |
| 4 | 3-{N—p-methoxybenzyl-N—[4'-bis(p-methoxybenzyl)aminobutyl]amino} propylaminobleomycin | A5TMDBZ(p) |
| 5 | 3-{N—p-methylbenzyl-N—[4'-bis(p-methylbenzyl)aminobutyl]amino} propylaminobleomycin | A5TMBZ(p) |
| 6 | 3-{N—cyclooctylmethyl-N—[4'-bis(cyclo-octylmethyl)aminobutyl]amino} propylaminobleomycin | A5TCO |
| 7 | 3-(4'-cycloundecanylmethylaminobutyl-amino)propylaminobleomycin | A5Cu |
| 8 | 3-{N—n-decyl-N—[4'-bis(n-decyl)-aminobutyl]amino}propylaminobleomycin | A5TDEC |
| 9 | 3-{N—n-pentyl-N—[4'-bis(n-pentyl) aminobutyl]amino}propylaminobleomycin | A5TPEN |
| 10 | 3-{N—m,p-dibenzyloxybenzyl-N—[4'-bis (m,p-dibenzyloxybenzyl)aminobutyl] amino}propylaminobleomycin | A5TDBZOBZ |
| 11 | 3-[N,N—dimethyl-N—(4'-dibenzylamino-butylamino]propylaminobleomycin | A5MMDBZ |
| 12 | 3-[N—methyl-N—benzyl-N—(4'-dibenzyl-aminobutyl)amino]propylaminobleomycin | A5MTBZ |

The compounds expressed by the general formula [I] according to this invention can be prepared in the manner described below.

Aminopropylaminobleomycin of the general formula [II]

$$[BX]-NH-(CH_2)_3-A'-(CH_2)_4-NH_2 \qquad [II]$$

wherein [BX] is as defined earlier, and A' represents a group of the formula

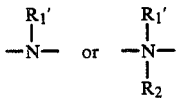

[in which R₁' represents a hydrogen atom or a lower alkyl group and R₂ is as defined earlier,] is reductively condensed with a carbonyl compound of the general formula [III]

$$R_5-CO-R_6 \qquad [III]$$

[wherein $R_5$ and $R_6$ each represents (i) a hydrogen atom, (ii) an alkyl group having 4 to 9 carbon atoms, (iii) a cycloalkyl group, or (iv) a phenyl group which may be substituted by one or more of a halogen atom, a lower alkyl group, a lower alkoxy group and a benzyloxy group,] thereby to obtain a compound expressed by the general formula [I].

Examples of the reducing agent for use in the condensation are borohydride compounds etc. such as sodium cyanoborohydride. The condensation may be also effected by catalytic reduction using a catalyst such as palladium carbon. When the carbonyl compound is used in an amount of 1 to 1.5 mols, a $BLMA_5$ deriv. having a hydrogen atom as $R_4$ is mainly obtained. When it is used in an amount of 3 or more mols, there is obtained a $BLMA_5$ deriv. in which $R_3$ and $R_4$ represent the same group.

The preferred amount of the carbonyl compound is 1.2 mols in order to obtain the $BLMA_5$ deriv. in which $R_4$ is hydrogen; or 10 mols to obtain the $BLMA_5$ deriv. in which $R_3$ and $R_4$ represent the same group; or 15 mols to obtain the $BLMA_5$ deriv. in which $R_1$, $R_2$ and $R_3$ represent the same group. When the compound of the formula [III] is a compound sparingly soluble in methanol, such as m,p-dibenzyloxybenzylaldehyde, its amount may be decreased, if the reaction time is prolonged.

The solvent used in the reaction is methanol, water, dimethylformamide, acetonitrile, or a mixture of these. The reaction temperature should preferably be 0° to 50° C. More specifically, it is preferred that the reaction temperature be 0° to 25° C. in order to obtain the derivative having a hydrogen atom as $R_4$; or 35° to 50° C. in case a ketone is used, or in case the desired derivative is one with $R_3$ and $R_4$ representing the same group and an aldehyde used has high steric hindrance or low solubility. The reaction time should preferably be 3 to 70 hours. If there is used an aldehyde high in steric hindrance or low in solubility, a prolonged reaction time is effective.

The so obtained derivative is isolated in the manner described below when the borohydride compound is used.

The reaction mixture is adjusted to a pH of 1 with hydrochloric acid, and stirred for 5 to 10 minutes at room temperature to decompose the excess reducing agent. Then, the reaction mixture is neutralized, and methanol is distilled off under reduced pressure. The excess aldehyde or ketone is removed by extraction with ether or butanol, followed by a desalting procedure. Namely, the aqueous layer is poured on a column of an adsorption resin, such as Amberlite ® XAD-2 (a product of Rohm & Haas), packed with the use of distilled water, so that the desired product is adsorbed to the column. The column is washed with distilled water to remove the salts, and is then eluted with acidic aqueous methanol, such as a 1/50N aqueous solution of hydrochloric acid-methanol (1:4 v/v). A blue fraction comprising a bleomycin derivative is collected, and if desired, neutralized with the anionic exchange resin Dowex ® 44 (OH type, a product of The Dow Chemical).

The fraction is concentrated under reduced pressure and lyophilized to obtain a blue crude powder of the derivative.

The following procedure is further carried out to increase the purity of the product.

The above powder is dissolved in distilled water, and the solution is poured on a column of CM Sephadex ® C-25 ($Na^+$ type: a product of Pharmacia Fine Chemicals) that has been equilibrated with a 1/20 mol acetic acid-sodium acetate buffer solution (pH: 4.5), so that the desired compound is adsorbed onto the column. The column is eluted by a linear concentration gradient involving sodium chloride added continuously to the same buffer solution to raise the sodium concentration to up to 1.0 mol gradually. If the desired fraction is found to contain impurities, this chromatography may be followed by chromatography using an adsorption resin such as Amberlite ® XAD-2. In this case, an aqueous solution of the crude substance is poured on a column of the resin packed with the use of a buffer solution such as a 4% aqueous solution of ammonium acetate, thereby adsorbing the desired product onto the column. The column is eluted by a linear concentration gradient involving methanol added continuously to the same buffer solution to gradually increase the methanol concentration. Usually, the unreacted starting materials come out the most quickly, followed by the derivative in which $R_4$ is a hydrogen atom, the derivative in which $R_3$ and $R_4$ represent the same group, and the derivative in which $R_1$, $R_3$ and $R_4$ represent the same group in that order. It is therefore possible to separate these compounds by using an ultraviolet ray absorption monitor. If the fraction comprising the desired product is found to contain impurities, the above-described chromatography may be carried out again to remove them completely.

The thus obtained fraction comprising the desired compound is distilled under reduced pressure to remove methanol. Then, the residue is desalted by the desalting method using Amberlite ® XAD-2 that has been employed earlier. The desalted substance is lyophilized to obtain a copper-containing $BLMA_5$ deriv. as a blue amorphous powder. The resulting copper-containing $BLMA_5$ deriv. is deprived of copper by a known methods, say, one using EDTA (U.S. Pat. No. 3,929,993) to obtain a copper-free derivative.

An example of this procedure will be described below. The copper-containing compound is dissolved in distilled water, and the solution is poured on a column of Amberlite ® XAD-2 packed with the use of distilled water, thereby adsorbing the compound onto the column. The column is washed with an aqueous solution comprising sodium chloride and 5% disodium ethylenediaminetetraacetate (referred to hereinafter as EDTA 2Na) so that copper ions may be carried away with EDTA 2Na. The $BLMA_5$ deriv. (copper-free) is thus left on the resin of the column. The column is washed with sodium chloride to remove EDTA 2Na, and further washed with distilled water. Finally, the column is eluted with acidic aqueous methanol, such as a 1/50N aqueous solution of hydrochloric acid-methanol (1:4 v/v), and fractions showing maximum absorption at a wavelength of about 290 millimicrons are combined. The combined fraction is adjusted to a pH of 6.0 with Dowex ® 44 (OH type: a product of The Dow Chemical), then concentrated under reduced pressure, and lyophilized to obtain a copper-free hydrochloride of the $BLMA_5$ deriv. as a white amorphous powder.

The use of an aqueous solution of sulfuric acid in place of the aqueous solution of hydrochloric acid in the above procedure would give a sulfate of the derivative. The desired salt can thus be obtained by selecting the type of the acid for use in the above-described elution step.

The BLMA5 deriv. produced by the above-mentioned method was hydrolyzed in a 6N aqueous solution of hydrochloric acid for 20 hours at 150° C. As a result, there were detected an amine and decomposition products common to BLMs, i.e., L-threonine, β-amino-β-(4-amino-6-carboxy-5-methyl-pyrimidin-2-yl) propionic acid, 4-amino-3-hydroxy-2-methyl-n-pentanoic acid, β-hydroxy-L-histidine, β-amino-L-alanine, and 2'-(2-aminoethyl)-2,4'-bithiazole-4-carboxylic acid. Upon methanolysis using Amberlist 15, the same methylglycoside of 3-O-carbamoyl-D-mannose or L-gulose as in bleomycin was detected by gas chromatography.

The above findings prove that BLMA5 deriv. produced by the method of this invention have a chemical structure expressed by the aforementioned formula [I].

The compounds of the aforementioned formula [II] include, for example, the following:
(1) 3-(4'-aminobutylamino)propylaminobleomycin (BLMA5)
(2) 3-[N,N-dimethyl-N-(4'-aminobutyl)amino]-propylaminobleomycin (A5MMHH)
(3) 3-[N-methyl-N-benzyl-N-(4'-aminobutyl)amino]-propylaminobleomycin (A5MBZHH)

The letters in parentheses stand for abbreviations.

The compounds of the aforementioned formula [III] include, for example, benzaldehyde, p-chlorobenzaldehyde, m,p-dichlorobenzaldehyde, p-methylbenzaldehyde, p-methoxybenzaldehyde, m,p-dibenzyloxybenzaldehyde, cyclooctylaldehyde, cycloundecanoylaldehyde, n-valeric aldehyde, and n-capric aldehyde.

The compounds of the general formula [II] are synthesized in the manner described below.

The method disclosed in U.S. Pat. No. Re. 30,451 is used to obtain them. It comprises cultivating a bleomycin-producing strain of Steptomyces verticillus, such as Streptomyces verticillus NK-68-144 (American Type Culture Collection No. 31307), in the copresence of an amine expressed by the general formula [IV]

NH$_2$—(CH$_2$)$_3$—A'—(CH$_2$)$_4$-NH$_2$      [IV]

wherein A' is as defined earlier. The compounds obtained by this method include, for example, BLM-A5.

Alternatively, the compounds of the general formula [II] can be synthesized in the following way if A' in this formula denotes a quaternary salt:

An amino-protecting group, such as tert-butoxycarbonyl group, is introduced by a known method into the primary amino group of the terminal amine segment of BLM-A5 obtained in the above-mentioned technique, thereby to obtain a compound of the general formula [V]

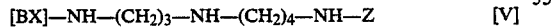
[BX]—NH—(CH$_2$)$_3$—NH—(CH$_2$)$_4$—NH—Z      [V]

in which [BX] is as defined previously, and Z represents a protective group.

In case R$_1$ and R$_2$ represent the same group the compound of the formula [V] is reacted with a halide of the general formula [VI]

R$_1$"X      [VI]

in which R$_1$" represents a lower alkyl group, and X represents a halogen atom, from a quaternary salt of the general formula [VII]

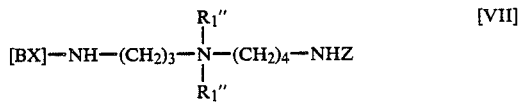

$$[BX]-NH-(CH_2)_3-\underset{\underset{R_1''}{|}}{\overset{\overset{R_1''}{|}}{N}}-(CH_2)_4-NHZ \qquad [VII]$$

in which [BX] is as defined previously, and R$_1$" and Z are as defined above. Then, the quaternary salt is subjected to a known method, for example, one using 6N hydrochloric acid with cooling with ice, if Z is a tert-butoxycarbonyl group. This step removes the tert-botoxycarbonyl group to obtain the compound of the general formula [II]. An example of the compound obtained by this method is A5MMHH.

In case R$_1$ and R$_2$ are different groups, the compound of the formula [V] is condensed reductively with the compound of the general formula [III] to form a compound of the general formula [VIII]

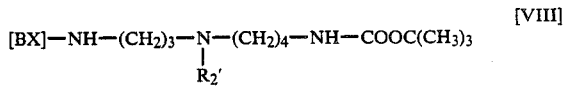

$$[BX]-NH-(CH_2)_3-\underset{\underset{R_2'}{|}}{N}-(CH_2)_4-NH-COOC(CH_3)_3 \qquad [VIII]$$

in which [BX] and Z are defined earlier, and R$_2$' represents a benzyl group.

The compound of the formula [VIII] is reacted with the compound of the formula [VI] to form a quaternary salt of the general formula [IX]

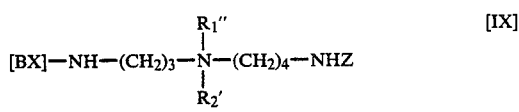

$$[BX]-NH-(CH_2)_3-\underset{\underset{R_2'}{|}}{\overset{\overset{R_1''}{|}}{N}}-(CH_2)_4-NHZ \qquad [IX]$$

in which [BX], R$_1$", R$_2$' and Z are as defined earlier. Then, the protective group is removed by the aforementioned method to obtain the compound of the general formula [II]. An example of the compound obtained by this method is A5MBZHH.

Table 2 shows the physiocochemical properties of typical aminopropylaminobleomycin derivatives according to the present invention.

TABLE 2

| Comp. No. | Abbreviation | UV absorption maximum of copper-free compound mμ (E 1%/1 cm) | Thin-layer chromatography of copper-containing compound (Rf value) *1 | Electrophoresis of copper-containing compound (Rm value) *2 |
|---|---|---|---|---|
| 1 | A5TBZ | 292 (89) | 0.80 | 1.07 |
| 2 | A5TC1BZ(p) | 293 (78) | 0.75 | 0.92 |
| 3 | A5TDC1BZ(m,p) | 294 (75) | 0.67 | 0.82 |
| 4 | A5TMDBZ(p) | 290 (104) 281 (107) | 0.79 | 0.98 |

TABLE 2-continued

| Comp. No. | Abbreviation | UV absorption maximum of copper-free compound mμ (E 1%/1 cm) | Thin-layer chromatography of copper-containing compound (Rf value) *1 | Electrophoresis of copper-containing compound (Rm value) *2 |
|---|---|---|---|---|
| 5 | A5TMBZ(p) | 292 (77) | 0.76 | 0.95 |
| 6 | A5TCO | 292 (97) | 0.54 | 0.92 |
| 7 | A5Cu | 292 (76) | 0.58 | 0.97 |
| 8 | A5TDEC | 291 (68) | 0.53 | 0.27 |
| 9 | A5TPEN | 292 (83) | 0.77 | 0.98 |
| 10 | A5TDBZOBZ | 285 (88) | 0.60 | 0.23 |
| 11 | A5MMDBZ | 292 (86) | 0.84 | 1.11 |
| 12 | A5MTBZZ | 292 (91) | 0.83 | 1.04 |

*1: Silica Gel 60 F 254 Silanized ® (Merck), methanol-6% ammonium acetate (80:20 v/v)
*2: Avicel SF ® (FMC), formic acid-acetic acid-water (27:75:900 v/v), 800 V, 15 min., alanine = 1.0

The following description shows the biological properties of the compounds of this invention that were investigated using typical examples of these compounds.

(1) Antibacterial activity against *Mycobacterium smegmatis* ATCC607 and *Bacillus subtilis*

The above activity ws determined by the agar cylinder plate method using the above microorganisms. The standard substance bleomycin A2 (a copper-free compound) had a titer of 1,000 mcg potency/mg.

(2) Growth-inhibiting effect on HeLa S3 cell cultured

A culture medium (10% calf serum-containing MEM) in a plastic dish was inoculated with HeLa S3 cells, and a bleomycin compound was added 2 days later. Incubation was continued for a further 3 days, and then the number of viable cells was counted. Growth inhibitory rate was calculated from the following equation:

$$\text{Growth inhibitory rate (\%)} = 100 \times (B-A)/(B-C)$$

where A is the final bacterial cell count 3 days after addition of the test sample, B is the final bacterial cell count in the control involving no addition of the test sample, and C is the bacterial cell count at the time of addition of the test sample.

$ID_{50}$, the concentration producing a growth inhibitory rate of 50%, was estimated from the curve of the concentration of the test sample Vs. the growth inhibitory rate.

The results of the studies (1) and (2) are shown in Table 3.

TABLE 3

| Comp. No. | Abbreviation | Antibacterial titer of copper-compound (mcg potency/mg) Test organism | | $ID_{50}$ of copper-free compound mcg/ml |
|---|---|---|---|---|
| | | *Mycobacterium smegmatis* ATCC 607 | *Bacillus subtilis* | |
| 1 | A5TBZ | 17360 | 400 | 0.40 |
| 2 | A5TC1BZ(p) | 613 | 129 | 0.73 |
| 3 | A5TDC1BZ (m,p) | 217 | 43 | 0.20 |
| 4 | A5TMDBZ(p) | 11109 | 197 | 0.54 |
| 5 | A5TMBZ(p) | 4560 | 203 | 0.38 |
| 6 | A5TCO | 530 | 61 | 0.064 |
| 7 | A5Cu | 24240 | 7330 | 0.16 |
| 8 | A5TDEC | 295 | 75 | 0.26 |
| 9 | A5TPEN | 57408 | 3520 | 0.28 |
| 10 | A5TDBZOBZ | 136 | 6 | 0.04 |
| 11 | A5MMDBZ | 20160 | 2528 | 0.12 |
| 12 | A5MTBZ | 13733 | 832 | 0.65 |

(3) Pulmonary toxicity (fibrosis of the lung) in mice

ICR mice (male, 15-week-old) were used in groups of 10 each. The dose of each test compound was 5 mg/kg injected intraperitoneally once daily for 10 consecutive days. After the administration of the compound was completed, the animals were reared for 5 weeks for observation. Then, the animals were killed and autopsied so that the incidence and grade of pulmonary fibrosis were examined.

The incidence of pulmonary fibrosis was expressed as the number of mice developing pulmonary fibrosis in the group of mice administered the test compound. The grade of pulmonary fibrosis was expressed as the total score for pulmonary fibrosis divided by the total number of specimens.

The results are shown in Table 4.

TABLE 4

| | Incidence (%) | | Grade (%) | |
|---|---|---|---|---|
| Comp. No. | Number of mice with pulmonary fibrosis/ Number of mice in the treatment group | Ratio | Total score for pulmonary fibrosis/Total specimens | Ratio |
| 1 | 0/10 (0) | 0.00 | (0/30 (0) | 0.00 |
| 2 | 0/10 (0) | 0.00 | (0/30 (0) | 0.00 |
| 3 | 0/10 (0) | 0.00 | (0/30 (0) | 0.00 |
| 4 | 0/10 (0) | 0.00 | (0/30 (0) | 0.00 |
| 5 | 0/10 (0) | 0.00 | (0/30 (0) | 0.00 |
| 6 | 0/10 (0) | 0.00 | (0/30 (0) | 0.00 |
| 7 | 0/10 (0) | 0.00 | (0/30 (0) | 0.00 |
| 8 | 0/10 (0) | 0.00 | (0/30 (0) | 0.00 |
| 9 | 0/10 (0) | 0.00 | (0/30 (0) | 0.00 |
| 10 | 0/10 (0) | 0.00 | (0/30 (0) | 0.00 |
| 12 | 0/10 (0) | 0.00 | (0/30 (0) | 0.00 |
| A5 | 5/10 (50) | 0.71 | (5/30 (0.17) | 0.29 |

The score in the table is defined as follows:
0 point: No fibrosis:
1 point: Accumulation of exudate in the alveoli, and fibrosis-like changes seen in the alveolar septum.
2 points: Fibrosis seen at several sites.
4 points: Sporadic fibrosis.
6 points: Extensive fibrosis (fibrosis seen in more than 170 of the total region).

The ratio in the table represents the ratio of the incidence of the test compound to that of bleomycin complex, or the ratio of the grade of the test compound to that of bleomycin complex.

The above results show that the compound of the present invention has a potent growth inhibitory activity against HeLa S3 cells cultured, an excellent antibacterial activity, and no pulmonary toxicity. This fact clearly suggests the clinical usefulness of this compound.

The present invention will be described in greater detail with reference to the following Examples.

EXAMPLE 1

Step A:

1.0 g of 3-(4'-aminobutylamino)propylaminobleomycin trihydrochloride (a copper-containing compound) was dissolved in 30 ml of methanol, and 987.8 mg of benzaldehyde was added to the solution. Then, 78.0 mg of sodium boron cyanohydride was added. The mixture was reacted for 24 hours at room temperature, and then the pH of the reaction mixture was adjusted to 1.0 with the addition of a 6N aqueous solution of hydrochloric acid, followed by allowing the mixture to stand for 10 minutes, to terminate the reaction. The reaction mixture was neutralized with 1N sodium hydroxide, and distilled under reduced pressure to remove methanol. Distilled water was added to the residue to form a 50 ml mixture. The mixture was extracted with 50 ml of ether to remove the excess aldehyde.

The aqueous layer was poured on a 100 ml column of Amberlite ® XAD-2 (Rohm & Haas) packed with the use of 40% aqueous solution of ammonium acetate 2% aqueous solution of acetic acid (1:1 v/v) to adsorb the desired compound onto the column. The column was eluted by a linear concentration gradient involving 500 ml of methanol added continuously to 500 ml of the same buffer solution. The desired fraction (200 ml) eluted at a methanol concentration of about 75% was collected which showed absorption maximum at a wavelength in the vicinity of 290 millimicrons. This fraction was distilled under reduced pressure to remove methanol, and the resulting aqueous solution was poured on a 100 ml column of Amberlite ® XAD-2 (Rohm & Haas) packed with the use of distilled water, thereby to adsorb the desired compound onto the column. The column was washed with 150 ml of distilled water, and then eluted with a 1/50M aqueous solution of hydrochloric acid-methanol (1:4 v/v). A blue fraction comprising a bleomycin derivative was collected, and neutralized with the anionic exchange resin Dowex ® 44 (OH type, a product of The Dow Chemical). Then, the fraction was concentrated under reduced pressure, and lyophilized.

The so obtained powder was dissolved in 10 ml of distilled water, and poured ion a 100 ml column of CM Sephadex ® C-25 (Na+ type, a product of Pharmacia Fine Chemical) equilbrated with a 1/20M acetic acid-sodium acetate buffer solution (pH 4.5), thereby to adsorb the desired compount onto the column. The column was eluted using a linear concentration gradient involving sodium chloride added continuously to the same buffer solution to raise the sodium concentration to up to 1.0 mol gradually. In this case, the amount of the eluting solution was 550 ml. A blue fraction (120 ml) coming out at a sodium concentration of about 0.65 mol was collected, and desalted by the desalting method using Amberlite ® XAD-2 employed earlier. The desalted fraction was lyophilized to obtain 680 ml of copper-containing 3-[N-benzyl-N-(4'-dibenzylaminobutyl-)amino]-propylaminobleomycin as a blue amorphos powder (Yield: 60.5%).

Step B:

680 mg of the copper-containing compound obtained in Step A was dissolved in 18 ml of distilled water. The solution was poured on a 100 ml column of Amberlite XAD-2 packed with the use of distilled water, to adsorb the desired compound onto the column, so that copper contained in the compound might be removed. The column was washed with 300 ml of an aqueous solution comprising sodium chloride and 5% EDTA 2Na, and then washed with 100 ml of 2% sodium chloride and 150 ml of distilled water in this order. Finally, the column was eluted with a 1/50N aqueous solution of hydrochloric acid-methanol (1:4 v/v), and the fraction showing an absorption maximum at a wavelength of about 290 millimicrons was collected. The pH of the fraction was adjusted to 6.0 with Dowex 44 (OH type, a product of The Dow Chemical), and concentrated under reduced pressure, followed by lyophilization to obtain 645 mg of a copper-free trihydrochloride of 3-[N-benzyl-N-(4'-dibenzylaminobutyl)amino]-propylaminobleomycin (Compound No. 1) as a white amorphous powder (yield: 98.2%).

The ultraviolet absorption maximum wavelength of the resulting product as measured in distilled water was 292 m$\mu$, and the E 1%/1 cm corresponding to it was 89. The infrared absorption maximum wavenumbers (ch$^{-1}$) as measured by the KBr method were as follows:
3350, 2950, 1650, 1550, 1510, 1455, 1400, 1320, 1255, 1130, 1090, 1050, 970, 910, 805, 740, 695

Other physicochemical properties are shown in Table 2.

In the above procedure, 1185.4 mg of m,p-dibenzyloxybenzaldehyde was used as aldehyde, and the reaction was performed for 70 hours at 27° C. Thereafter, purification and copper removal were carried out by the same methods to obtain 664.8 mg of a copper-free trihydrochloride of 3-{N-m,p-dibenzyloxybenzyl-N-[4'bis(m,p-dibenzyloxybenzyl)aminobutyl]amino} propylaminobleomycin (Compound No. 10) as a colorless amorphous powder (yield: 43.6%).

This product had an ultraviolet absorption maximum wavelength, as measured in distilled water, of 285 m$\mu$, and its E 1%/1 cm corresponding to the wavelength was 88. The infrared absorption maximum wavenumbers (cm$^{-1}$) as measured by the KBr method were as follows:
3350, 2950, 1650, 1550, 1510, 1460, 1430, 1390, 1270, 1190, 1140, 1060, 1020, 910, 850, 810, 740, 690

In said procedure, 1305.3 mg of cyclooctanecarboxyaldehyde was used as aldehyde, and the reaction was performed for 16 hours at room temperature. Thereafter, purification and copper removal were carried out by the same methods to obtain 876.9 mg of a copper-free trihydrochloride of 3-{N-cyclooctylmethyl-N-8 4'bis(cyclooctylmethyl) aminobutyl]amino} propylaminobleomycin (Compound No. 6) as a colorless amorphous powder (yield: 73.5%).

The product had an ultraviolet absorption maximum wavelength, as measured in distilled water, of 292 m$\mu$, and an E 1% cm, corresponding to the wavelength, of 97. Its infrared absorption maximum wavenumbers (cm$^{-}$) as measured by the KBr method were as follows:
3350, 2925, 1650, 1550, 1520, 1450, 1400, 1330, 1260, 1190, 1140, 1100, 1060, 1020, 980, 910, 810

The same procedure as in this Example was carried out to prepare the compounds shown in Table 5.

TABLE 5

| Desired Comp. No. | Starting comp. of formula III | Number of equiv. of comp. III | Reaction time (hrs.) | Reaction temp. (°C.) | Yield (%) |
| --- | --- | --- | --- | --- | --- |
| 2 | p-Chlorobenzaldehyde | 15 | 24 | 22 | 46.8 |
| 3 | m,p-Dichlorobenzaldehyde | 15 | 24 | 22 | 68.7 |
| 4 | p-Methoxybenzaldehyde | 15 | 48 | 22 | 60.8 |
| 5 | p-Methylbenzaldehyde | 15 | 24 | 22 | 57.4 |
| 7 | Cycloundecanecarboaldehyde | 10 | 24 | 22 | 69.6 |
| 8 | n-Capric aldehyde | 15 | 16 | 22 | 55.0 |
| 9 | n-Valeric aldehyde | 15 | 16 | 22 | 57.9 |

EXAMPLE 2

Step A:

200 mg of 3-[N,N-dimethyl-N(4'-aminobutyl) amino]-proylaminobleomycin trihydrochloride (a copper-containing compound) was dissolved in 6 ml of methanol. 129.7 mg of benzaldehyde was added, and then 10.2 mg of sodium boron cyanohydride was added. The mixture was reacted for 16 hours at room temperature, whereafter treatment with hydrochloric acid, extraction with ether, and chromatography on an Amberlite ® XAD-2 column were performed in the same way as in Example 1. The resulting fraction was desalted by the Amberlite ® XAD-2 desalting method employed previously, and the desalted fraction was lyophilized to obtain 155.4 mg of copper-containing 3-[N,N-dimethyl-N-(4'-dibenzylaminobutyl) amino]-propylaminobleomycin as a blue amorphous powder. Yield: 70%.

Step B:

155.4 mg of the copper-containing compound obtained in Step A was dissolved in 10 ml of distilled water. The solution was desalted in the same way as in Step B of Example 1, and the resulting fraction was concentrated under reduced pressure. The residue was lylophilized to obtain 142.6 mg of a copper-free trihydrochloride of 3-[N,N-dimethyl-N-(4'-dibenzyl-aminobutyl) amino]propylaminobleomycin (Compound No. 11) as a white amorphous powder. Yield: 95%.

The product had an ultraviolet absorption maximum wavelength, as measured in distilled water, of 292 m$\mu$, and the corresponding E 1% cm of 86. Its infrared absorption maximum wavenumbers (cm$^{-1}$) as measured by the KBr method were as follows:

3325, 2950, 1660, 1540, 1490, 1450, 1400, 1330, 1260, 1190, 1100, 1060, 1020, 980, 800, 740, 695

In the above-described procedure, 200 mg of 3-[N-methyl-N-benzyl-N-(4'-aminobutyl) amino]-propylaminobleomycin trihydrochloride (a copper-containing compound) was used as the starting material, and reacted with 123.7 mg of benzaldehyde in the same way.

Then, purification and copper removal were performed in the same way to obtain 132 mg of copper-free trihydrochloride of 3-[N-methyl-N-benzyl-N-(4'-dibenzylaminobutyl) amino]propylanoblebleomycin (Compound No. 12) as a colorless amorphous powder. Yield: 61.8%.

The ultraviolet absorption maximum wavelength, as measured in distilled water, of the resulting product was 292 m$\mu$, and the corresponding E 1%/1 cm of 91. The infrared absorption maximum wavenumbers (cm$^{-1}$) as measured by the KBr method were as follows:

3375, 2950, 1640, 1540, 1500, 1450, 1390, 1320, 1250, 1190, 1130, 1050, 1020, 970, 900, 800, 740, 695

EXAMPLE 3

300 mg of 3-(4'-tert-butoxycarbonylaminobutylamino)-propylaminobleomycin dihydrochloride ( a copper-containing compound) was dissolved in 15 ml of methanol. 414.9 mg of tri-n-butylamine and 1271.3 mg of methyl iodide were added at 0° C., the system was reacted for 3 days. The reaction mixture was adjusted to a pH of 6 with glacial acetic acid, and the excess methyl iodide and methanol were distilled off under reduced pressure. Acetone was added to the residue to precipitate bleomycin. The precipitate was collected by filtration, and washed with acetone. The washed precipitate was dissolved in 2 ml of distilled water, and 2 ml of concentrated hydrochloric acid was added with the solution cooled with ice. The mixture was reacted as such for 90 minutes to remove the tert-butyloxycarbonyl group. the reaction mixture was neutralized with a 2N aqueous solution of potassium acetate, and the black brown precipitate formed was removed by filtration. The filtrate was poured on a 100 ml column of Amberlite ® XAD-2 (Rome & Haas) packed with the use of 4% aqueous solution of ammonium acetate-2% aqueous solution of acetic acid (1:1 v/v), thereby adsorbing the reaction product onto the column. The column was eluted by a linear concentration gradient having 500 ml of methanol added continuously to 500 ml of the same buffer solution.

The desired fraction showing an absorption maximum at a wavelength in the vicinity of 290 millimicrons was collected which was eluted at a methanol concentration of about 10%. This fraction was distilled under reduced pressure to remove methanol, and the resulting aqueous solution was poured on a 100 ml column of Amberlite ®XAD-2 (a product of Rohm & Haas) packed with the use of distilled water, so that the desired product might be adsorbed. The column was desalted with 125 ml of distilled water, and eluted with a 1/50N aqueous solution of hydrochloric acid-methanol (1:4 v/v). The blue fraction comprising the desired product was collected, and if desired, neutralized with the anionic exchange resin Dowex ® 44 (OH type, a product of The Dow Chemical). Then, the fraction was concentrated under reduced pressure, and lyophilized to obtain 211.0 mg of 3-[N,N-dimethyl-N-(4'-aminobutyl) amino]-propylaminobleomycin (A5MMHH) trihydrochloride (a copper-containing compond) a blue amorphous powder. Yield: 72%.

This product had an ultraviolet absorption maximum wavelengths, as measured in distilled water, of 293 and 243 m$\mu$, and the corresponding E 1%/1 cm's of 122 and 151, respectively. The infrared absorption maximum wavenumbers (cm$^{-1}$) as measured by the KBr method were as follows:

3300, 2975, 2950, 2900, 1715, 1670, 1580, 1460, 1400, 1340, 1300, 1200, 1140, 1100, 1080, 1020, 920, 880, 810, 770 740

EXAMPLE 4

300 mg of 3-(4'-tert-butoxycarbonylaminoburylamino) propylaminobleomycin dihydrochloride (a copper-containing compound) was dissolved in 10 ml of methanol, and 76 mg of benzaldehyde and 7.5 mg of sodium boron cyanohydride were added. The mixture was reacted for 24 hours at room temperature, and ether was added to precipitate bleomycin. The resulting blue precipitate was collected by filtration and washed with ether. Then, the washed substance was passed through a 100 ml column of Amberlite® XAD-2 (Rohm & Haas) packed with the use of distilled water, thereby adsorbing the reaction product onto the column. 150 ml of distilled water was flowed through the column, and then the column was eluted with a 1/50N aqueous solution of hydrochloric acid-methanol (1:4 v/v).

Blue fractions comprising the desired product were combined, and if desired, neutralized with the anionic exchange resin Dowex® 44 (OH type, a product of The Dow Chemical), followed by concentrating the neutralized fraction to dryness under reduced pressure. 15 ml of methanol was added to the residue, and the mixture was cooled to 0° C. 207.5 mg of tri-n-butylamine and 635.7 mg of methyl iodide were added, and the mixture was reacted for 3 days. The reaction mixture was treated and purified in the same way used in Example 4, and lyophilized to obtain 205 mg of a copper-containing trihydrochloride of 3-[N-methyl-N-benzyl-N-(4'-aminobutyl)-amino]propylaminobleomycin (A5MBZHH) as a blue amorphous powder. Yield: 66.7%.

The ultraviolet absorption maximum wavelengths, as measured in distilled water, of the product were 293 and 243 mμ, and the corresponding E 1%/1 cm's were 120 and 150, respectively. The infrared absorption maximum wavenumbers (cm$^{-1}$) as measured by the KBr method were as follows:

3350, 2950, 1715, 1660, 1560, 1460, 1400, 1330, 1300, 1250, 1200, 1140, 1100, 1060, 1010, 920, 880, 810, 770, 720, 700

Other physicochemical properties are shown in Table 6.

TABLE 6

| Compound synthesized (abbreviation) | UV absorption maximum of copper-containing compound (mμ, E 1%/1 cm) | Thin-layer chromatography of copper-containing comp. (Rf value) *1 | Electrophoresis of copper containing compound (Rm value) *2 |
|---|---|---|---|
| A5MMHH | 293 (122) 243 (151) | 0.80 | 1.17 |
| A5MBZHH | 293 (120) 243 (150) | 0.73 | 1.15 |
| Boc-A5 | 293 (140) 244 (173) | 0.62 | 0.90 |

*1, *2: Same as in the footnotes to Table 2.

REFERENTIAL EXAMPLE 1

1.5 g of 3-(4'-aminobutylamino) propylaminobleomycin trihydrochloride (a copper-containing compound) was dissolved in 60 ml of methanol. 690.1 mg of tri-n-butylamine and 203.2 mg of di-tert-butyl-dicarbonate were added to the solution with cooling with ice, and the reaction mixture was stirred for 4 hours. The reaction mixture was neutralized with glacial acetic acid, and distilled under reduced pressure to remove methanol. 20 ml of water was added to the residue to dissolve it, and the solution was poured on a 100 ml of column of Amberlite® XAD-2 (a product of Rohm & Haas) packed with the use of 4% aqueous solution of ammonium acetate-2% aqueous of acetic acid (1:1 v/v), thereby to adsorb the reaction product onto the column. The column was eluted by a linear concentration gradient method involving the continuous addition of 500 ml of methanol to 500 ml of the same buffer solution. 200 ml of the desired fraction showing an absorption maximum at a wavelength of about 290 millimicrons that came out at a methanol concentration of about 35% was collected. This fraction was distilled under reduced pressure to remove methanol, and the resulting aqueous solution was poured on a 100 ml of Amberlite® XAD-2 (a product of Rohm & Haas) packed with the use of distilled water, thereby adsorbing the desired product onto the column. The column was washed with 150 ml of distilled water, and eluted with a 1/50N aqueous solution of hydrochloric acid-methanol (1:4 v/v). The blue fraction comprising the resulting bleomycin derivative was collected, and neutralized with the anionic exchange resin Dowex® 44 (OH type, a product of The Dow Chemical). Then, the fraction was concentrated under reduced pressure, and lyophilized to obtain 687 mg of a copper-containing dihydrochloride of 3-N-(4'-tert-butyloxycarbonylaminobutyl)-aminopropylaminobleomycin (referred to as Boc-A5) as a blue amorphous powder. Yield 44%.

The ultraviolet absorption maximum wavelengths, as measured in distilled water, of the resulting product were 293 and 244 mμ, and the corresponding E 1%/1 cm's were 140 and 173, respectively. The infrared absorption maximum wavenumbers (cm$^{-1}$) as measured by the KBr method were as follows:

3350, 2950, 1710, 1670, 1560, 1460, 1400, 1360, 1330, 1290, 1250, 1170, 1130, 1100, 1060, 1010, 920, 880, 800, 760

Other physicochemical properties are shown in Table 6.

What is claimed is:

1. An aminopropylaminobleomycin derivative expressed by the following formula

[BX]—NH—(CH$_2$)$_3$—(CH$_2$)$_4$—B wherein [BX] represents a residue remaining after removing a hydroxyl group from the carboxyl group of bleomycinic acid, A represents a group of the formula

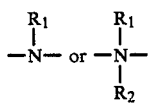

in which R$_1$ represents (i) a hydrogen atom, (ii) an alkyl group having 1 to 10 carbon atoms, or (iii) an methyl which may be substituted at least one of a phenyl group and a cycloalkyl group having 5 to 13 carbon atoms, said substituents being each unsubstituted or substituted in more than one position by one or more substituents selected from the class consisting of a halogen atom, a lower alkyl group having 1 to 4 carbon atoms, a lower alkoxy group having 1 to 4 carbon atoms or a benzyl group, B represents a group of the formula

in which $R_3$ and $R_4$ each represents (i) a hydrogen atom, (ii) an alkyl group having 5 to 10 carbon atoms, or (iii) a methyl which is substituted by at least one of a phenyl group and a cycloalkyl group, said substituents being each unsubstituted or substituted in more than one position by one or more substituents selected from the class consisting of a halogen atom, a lower alkyl group having 1 to 4 carbon atoms, a lower alkoxy group having 1 to 4 carbon atoms and a benzyloxy group, with the proviso that at least one of $R_3$ and $R_4$ is a group other than a hydrogen atom, and a pharmaceutically effective inorganic acid addition salt thereof, provided that when A is NH and one of of $R_3$ and $R_4$ is hydrogen, the other $R_3$ or $R_4$ is not a methyl substituted by one phenyl group.

2. An aminopropylaminobleomycin derivative or the salt thereof as set forth in claim 1, wherein $R_1$ represents a hydrogen atom, methyl, pentyl, decyl, cyclooctylmethyl, benzyl, chlorobenzyl, dichlorobenzyl, methylbenzyl, methoxybenzyl, or dibenzyloxybenzyl; and $R_2$ represents methyl, or benzyl; $R_3$ represents hydrogen atom, pentyl, decyl, cyclooctylmethyl, cycloundecanylmethyl, benzyl, chlorobenzyl, dichlorobenzy, methoxybenzyl, methylbenzyl, or dibenzyloxybenzyl; $R_4$ represents pentyl, decyl, cyclooctyl, cycloundecanyl, benzyl, chlorobenzyl, dichlorobenzyl methoxybenzyl, methylbenzyl, or dibenzyloxybenzyl, provided that when A is NH and one of of $R_3$ and $R_4$ is hydrogen, the other $R_3$ or $R_4$ is not a methyl substituted by one phenyl group.

3. An aminopropylaminobleomycin derivative or the salt thereof as set forth in claim 1, wherein A represents

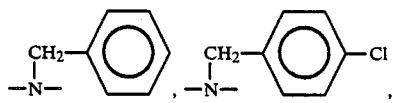

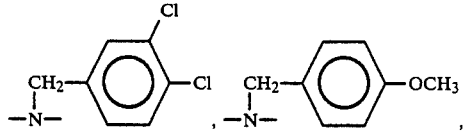

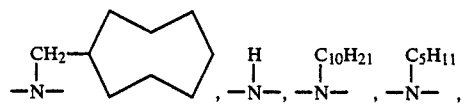

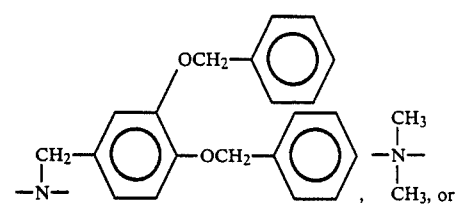

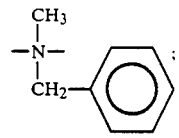

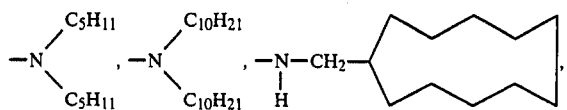

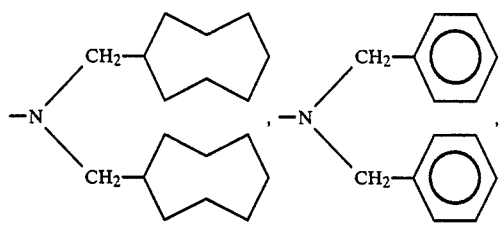

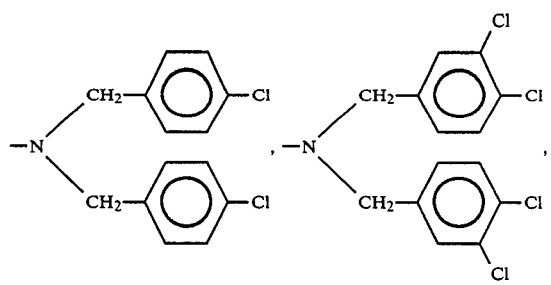

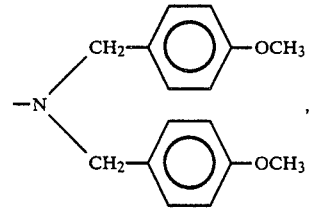

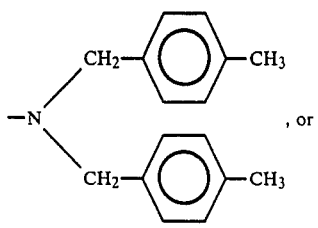

-continued

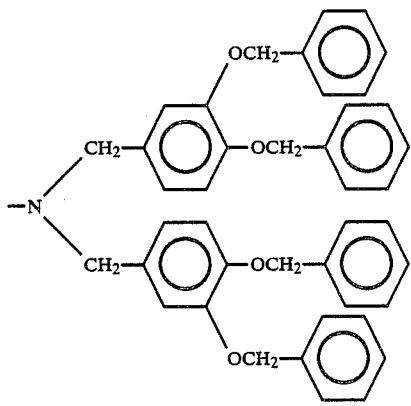

provided that when A is NH and one of of $R_3$ and $R_4$ is hydrogen, the other $R_3$ or $R_4$ is not a methyl substituted by one phenyl group.

4. An aminopropylaminobleomycin expressed by the following formula

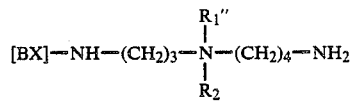

wherein [BX] represents a residue remaining after removing a hydroxyl group from the carboxyl group of bleomycinic acid, $R_1''$ represents a lower alkyl group, and $R_2$ represents lower alkyl group or a benzyl group, and a pharmaceutically effective inorganic acid addition salt thereof.

5. An aminopropylaminobleomycin of the salt thereof as set forth in claim 4, wherein $R_1''$ represents methyl; and lower alkyl in $R_2$ represents methyl.

* * * * *